United States Patent [19]

Lang et al.

[11] Patent Number: 5,340,366
[45] Date of Patent: Aug. 23, 1994

[54] HAIR DYE COMPOSITIONS AND PROCESS COMPRISING AND UTILIZING A COMBINATION OF ISATIN AND AMINOPYRIMIDINE DERIVATIVES

[75] Inventors: Gerard Lang, Saint-Gratien; Jean Cotteret, Verneuil-sur-Seine, both of France

[73] Assignee: L'Oreal, Paris, France

[21] Appl. No.: 136,125

[22] Filed: Oct. 15, 1993

Related U.S. Application Data

[63] Continuation of Ser. No. 845,587, Mar. 4, 1992, Pat. No. 5,279,616.

[30] Foreign Application Priority Data

Mar. 5, 1991 [FR] France ................. 91 02614

[51] Int. Cl.$^5$ ................. A61K 7/13
[52] U.S. Cl. ................. 8/406; 8/408; 8/409; 8/423; 548/485
[58] Field of Search ................. 8/405, 406, 408, 409, 8/410, 423, 429; 548/485

[56] References Cited

U.S. PATENT DOCUMENTS

| | | | |
|---|---|---|---|
| 4,013,404 | 3/1977 | Parent et al. | 8/11 |
| 4,168,953 | 9/1979 | Rose | 8/423 |
| 4,226,595 | 10/1980 | Rose et al. | 8/406 |
| 4,322,212 | 3/1982 | Konrad et al. | 8/423 |
| 4,750,908 | 6/1988 | Rosenbaum et al. | 8/429 |
| 4,921,503 | 5/1990 | Anderson et al. | 8/405 |

FOREIGN PATENT DOCUMENTS 0359465 3/1990 European Pat. Off. .

OTHER PUBLICATIONS

French Search Report of FR 91 02614.

*Primary Examiner*—Paul Lieberman
*Assistant Examiner*—Caroline L. Dusheck
*Attorney, Agent, or Firm*—Cushman, Darby & Cushman

[57] ABSTRACT

A process for dyeing keratinous fibers involves applying to the fibers, at least one compound of formula

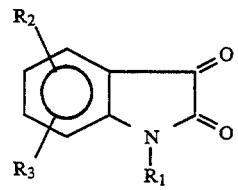

wherein $R_1$ represents hydrogen, alkyl, acetyl, benzoyl, phenyl or carboxylalkyl and $R_2$ and $R_3$ represent hydrogen, alkyl, hydroxyl, halogen, nitro, alkyl phenyl, phenyl or alkoxy, and an aminopyrimidine of the formula

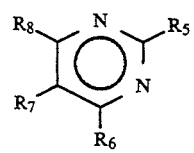

wherein $R_5$ represents hydrogen, hydroxyl or

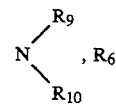

represents hydroxyl or

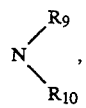

$R_7$ represents H or $NH_2$, $R_8$ represents

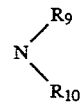

and $R_9$ and $R_{10}$ represent hydrogen, alkyl, $(CH_2)_p$-Z wherein p is 1 to 4 and Z represents OH, halogen, $NH_2$, NHR' or NHR'R" wherein R' and R" represent alkyl or together form a heterocycle, with the proviso that one of $R_5$ to $R_8$ represents $NH_2$.

13 Claims, No Drawings

HAIR DYE COMPOSITIONS AND PROCESS COMPRISING AND UTILIZING A COMBINATION OF ISATIN AND AMINOPYRIMIDINE DERIVATIVES

This is a continuation of application Ser. No. 07/845,587, filed Mar. 4, 1992, U.S. Pat. No. 5,279,616.

The present invention relates to a process for dyeing keratinous fibers, especially human hair, combining isatin or one of its derivatives with an aminopyridine or aminopyrimidine, as well as to the dyeing agents employed.

In direct dyeing of hair, that is to say in a dyeing process not employing the process of development of the dyes by oxidative means, the use of 2,3-indolinedione, also known as isatin, as a yellow base dye has already been proposed in French Patent No. 2,588,473.

European Application No. 0,359,465 then proposed a direct dyeing process employing isatin or one of its derivatives in combination with disubstituted aminobenzene derivatives.

The applicants have just discovered, surprisingly, a new dyeing process combining isatin or its derivatives with dyes of the aminopyridine or aminopyrimidine type, enabling a wide range of hues to be obtained, the latter being more resistant to shampooing and to perspiration than those obtained with the direct dyeing processes employing the known amino derivatives of the prior art. The colorations obtained are, in addition, stable to light, adverse weather conditions and chemical agents.

The subject of the present invention is hence a process for dyeing keratinous fibers, consisting in applying isatin or one of its derivatives and an aminopyridine or aminopyrimidine on the fibers either simultaneously in the form of a mixture prepared immediately before use, or successively.

A subject of the invention also consists of a two-component dyeing agent.

Other subjects will become apparent in the light of the description.

The process for dyeing keratinous fibers, especially human hair, according to the present invention, is essentially characterized in that it entails the application on the said fibers of a component (A) consisting of a composition containing, in a medium suitable for dyeing, at least one compound of the following formula (I):

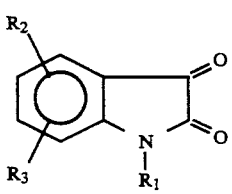

in which:

$R_1$ denotes a hydrogen atom or a $C_1$–$C_6$ alkyl, acetyl, benzoyl, phenyl or $C_1$–$C_4$ carboxyalkyl radical;

$R_2$ and $R_3$, independently of one another, denote a hydrogen atom, a $C_1$–$C_6$ alkyl, a hydroxyl, a halogen atom, a nitro group, a ($C_1$–$C_6$ alkyl)phenyl, phenyl or a $C_1$–$C_4$ alkoxy;

and a component (B) consisting of a composition containing, in a medium suitable for dyeing, at least one aminopyridine of the following formula (II):

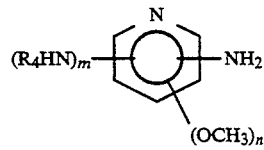

in which:

$R_4$ denotes a hydrogen atom or a $\beta$-hydroxyethyl group;

n=0, 1 or 2, and m =0 or 1;

as well as its cosmetically acceptable salts, or alternatively one aminopyrimidine of formula (III):

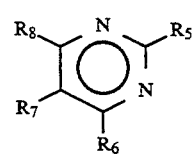

in which:

$R_5$ denotes a hydrogen atom, a hydroxyl group or a group

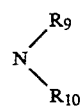

$R_6$ denotes a hydroxyl group or a group

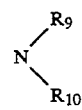

$R_7$ denotes H or $NH_2$,
$R_8$ denotes a group

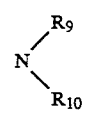

$R_9$ and $R_{10}$, independently of one another, representing a hydrogen atom, a $C_1$–$C_4$ alkyl, a group $(CH_2)_p$-Z, where p=1 to 4 and Z represents OH, halogen, $NH_2$, NHR′ or NHR′R″ where R′ and R″ denote a $C_1$–$C_4$ alkyl or form a heterocycle with the nitrogen atom to which they are attached;

with the proviso that one of the groups $R_5$ to $R_8$ denotes $NH_2$;

as well as its cosmetically acceptable salts.

For the formulae (I), (II) and (III) above, as $C_1$–$C_4$ alkyl radicals, methyl, ethyl, propyl, butyl, isopropyl, isobutyl and tert-butyl may be mentioned;

the $C_1$–$C_6$ alkyl radicals comprise, apart from those mentioned above, pentyl (linear and branched) and hexyl (linear and branched) radicals.

As $C_1$–$C_4$ alkoxy radicals, methoxy, ethoxy, propoxy and butoxy may be mentioned.

As hydroxyalkyl radicals, 2-hydroxyethyl and 2- or 3-hydroxypropyl may be mentioned.

As polyhydroxyalkyl radicals, 2,3-dihydroxypropyl and 3,4-dihydroxybutyl may be mentioned.

The heterocycles formed with the nitrogen atom are preferably piperidino, morpholino or piperazino rings.

The cosmetically acceptable salts are preferably chosen from the hydrochlorides, hydrobromides and sulphates.

The process according to the invention may be carried out without the participation of an oxidising agent other than air.

The dyeing process described above leads to the formation of a Schiff's base, either on mixing the component (A) with the component (B), or in situ in the keratinous fiber on sequential application of the components (A) and (B). This Schiff's base is of the formula:

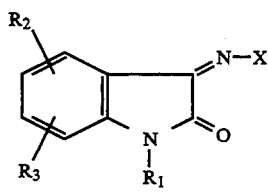
(IV)

in which X denotes:

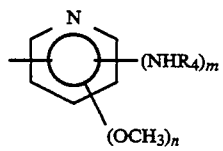
a)

where $R_4$, m and n have the meanings stated above for the formula (II),

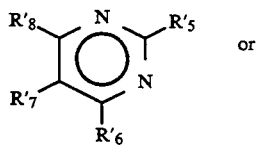
b)

where $R'_5$ denotes H, OH,

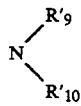

or a covalent bond,
$R'_6$ denotes OH,

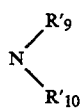

or a covalent bond,
$R'_7$ denotes H or a covalent bond, and
$R'_8$ denotes

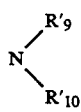

or a covalent bond, $R'_9$ and $R'_{10}$ having the same meanings as $R_9$ and $R_{10}$, one of the two being, however, other than a hydrogen atom, with the proviso that only one of the substituents $R'_5$ to $R'_8$ represents a covalent bond.

Among the compounds of formula (I), isatin may be mentioned more especially.

Preferred compounds of formula (II) or (III) are chosen from:
2,3-diaminopyridine
3,4-diaminopyridine
2-aminopyridine
5,6-diamino-2,4-dihydroxypyrimidine,
4,6-diaminopyrimidine,
2,6-dimethoxy-3,5-diaminopyridine, and
6-methoxy-2,3-diaminopyridine.

In addition to these preferred compounds, more especially preferred compounds are:
2,5-diaminopyridine, and
2,4,5,6-tetraaminopyrimidine.

According to the process of the present invention, the compounds of formula (I) are preferably present in the component (A) in proportions of between 0.01 and 5% by weight, and more especially between 0.25 and 2% by weight, relative to the total weight of the component (A) or of the components (A) +(B), and the compounds of formula (II) or (III) are present in the component (B) in proportions preferably of between 0.01 and 5% by weight, and especially between 0.25 and 2% by weight, relative to the total weight of the component (B) or of the components (A)+(B).

The components (A) and (B) which are usable according to the invention are more or less thickened aqueous or anhydrous liquid compositions, creams, aqueous or anhydrous gels, oils or powders to be diluted with a liquid at the time of use, also known as "cataplasms".

In a first embodiment of the invention, the cosmetic medium suitable for dyeing is aqueous and has a pH which can vary between 2 and 10, and preferably between 3 and 9.5; it is adjusted to the desired value using alkalinizing agents or acidifying agents which are known per se.

These compositions can contain anionic, cationic, nonionic or amphoteric surfactants or mixtures thereof. These surfactants are present in the compositions according to the invention in proportions of between 0.1 and 55% by weight, and preferably between 1 and 40% by weight, relative to the total weight of each composition.

These aqueous compositions can contain organic solvents, among which lower alkanols such as ethanol or isopropanol, polyols such as glycerol, glycols or glycol ethers such as ethylene glycol, propylene glycol, ethylene glycol monobutyl ether and diethylene glycol monoethyl ether and monomethyl ether, as well as similar products or mixtures thereof, may be mentioned as an example.

These solvents are preferably used in proportions ranging from 1 to 60% by weight, and more especially from 3 to 30% by weight, relative to the total weight of each composition.

These compositions may be thickened with agents chosen from sodium alginate, gum arabic, guar or carob gum, xanthan gum, scleroglucans, pectins, cellulose derivatives and various polymers having a thickening function, such as acrylic acid derivatives. It is also possible to use inorganic thickening agents such as bentonite.

These thickening agents are preferably present in proportions of between 0.1 and 5% by weight, and especially between 0.5 and 3% by weight, relative to the total weight of each composition.

These compositions can also contain artionic, nonionic, cationic or amphoteric polymers or mixtures thereof, in proportions of 0.1 to 5% by weight relative to the total weight of each composition.

These compositions can naturally contain any other adjuvants customarily used in compositions for dyeing hair, such as penetrating agents, sequestering agents, antioxidants, buffers, perfumes, dyes, and the like.

A preferred form of the invention consists in using an anhydrous medium as described in French Patent No. 2,526,031.

Anhydrous medium is understood to mean a medium containing not more than 1% of water.

The anhydrous medium consists, according to this variant of the invention, of a mixture of at least one anhydrous solvent and one or more anhydrous surfactants, such that these compositions contain at least 15% of solvent and at least 20% of surfactant.

The solvents used are cosmetically acceptable solvents chosen from $C_2$–$C_{20}$ saturated monohydric alcohols such as ethanol, isopropanol, cetyl alcohol or octyldodecanol; polyols such as alkylene glycols, for example ethylene glycol, propylene glycol, glycerol, diethylene glycol; glycol ethers such as mono-, di- and triethylene glycol monoalkyl ethers, such as for example ethylene glycol monoethyl ether, ethylene glycol monobutyl ether, diethylene glycol monoethyl ether; esters such as, for example, ethylene glycol monomethyl ether acetate, ethylene glycol monoethyl ether acetate; and esters of fatty acids and saturated lower alcohols, such as isopropyl myristate or palmirate.

Especially preferred compositions contain a solvent chosen from ethanol, cetyl alcohol, propylene glycol, ethylene glycol monoethyl ether or ethylene glycol monobutyl ether.

The surfactants used in this embodiment are chosen from anhydrous surfactants of the anionic, nonionic, cationic or amphoteric type or mixtures thereof. Polyoxyethylenated fatty alcohols, polyoxyethylenated alkylphenols or naphthols, monoalkyltrimethylammonium halides, dialkyldimethylammonium halides, soaps and polyglycerolated fatty alcohols may be mentioned more especially. Preferred surfactants are nonionic surfactants.

These compositions can contain an anhydrous alkaline or acidifying agent such as, for example, citric acid, ascorbic acid, acetic acid, lactic acid and alkanolamines such as, preferably, those which are completely substituted on the amine group, for example dimethylaminoethanol.

Apart from the compounds described above, the anhydrous compositions according to the invention can contain many additives which are usable in cosmetics, provided only that they contain less than 1% of water. Among these additives, perfumes, thickening agents, treating agents, antioxidants, vegetable or mineral oils, preservatives and organic salts may be mentioned.

These compositions may be applied as they are on wet hair, or be diluted at the very last moment before use. In the latter case, at the time of dyeing, the compositions according to the invention are diluted with an aqueous solution in such a way that the ratio of the composition according to the invention to the aqueous solution is between 0.25 and 2. The aqueous solution can consist of pure water, but also of any other more or less thickened complex aqueous liquid such as, for example, a vehicle customarily used in dyeing compositions for hair.

In this case, the components of the cosmetic medium can be all types of cosmetically acceptable ingredients, anhydrous or otherwise, customarily used in this type of composition and described in a general manner above.

Another mode of use of the components (A) and/or (B) according to the invention consists of use in the form of cataplasms, that is to say in the form of powder to be diluted with a liquid at the time of use.

In this embodiment, the dyes are prepared in the form of powder which is stable on storage, and introduced into a solid medium which can consist of powders, flours or amylaceous or mucilaginous substances which are diluted at the time of use with an appropriate liquid so as to form a mixture having a suitable consistency for application on the head.

The powders or flours used in this type of composition generally consist of insoluble substances such as silicas, clays and plants powdered after solvent-extraction of their active principles.

The liquid can consist of water or mixtures of water and cosmetically acceptable solvents such as alcohols or glycols, or alternatively of oils.

The liquid mixture is added to the powder in proportions such that, after mixing, a paste having a viscosity of between 0.3 and 5 Pa.s is obtained.

A subject of the invention consists of a dyeing agent for keratinous fibers, especially human hair, characterised in that it consists of components (A) and (B) as defined above, stored in separate form.

The components (A) and (B) are designed either to be mixed at the very last moment before use, or to be applied successively on the fibers to be treated.

According to an embodiment, the different components (A) and (B) may be packaged in a multicompartment device, also known as a "dyeing kit", containing all the components designed to be applied for a single dyeing treatment on the keratinous fibers, especially hair, in successive applications with or without premixing.

Such devices can possess a first compartment containing the component (A) containing isatin or its derivatives of formula (I), and a second compartment containing the component (B) containing the aminopyridine of formula (II) or the aminopyrimidine of formula (III).

Another variant can also consist in storing the component (A) or the component (B) in an anhydrous solvent medium, and in providing a third compartment containing a cosmetically acceptable aqueous medium suitable for dyeing. In this case, the contents of the third compartment are mixed at the very last moment before use into one or other or both compartments containing the anhydrous components (A) and (B), or else the three compartments are mixed before use.

According to a variant, the process of the invention consists in mixing the component (A) with the component (B) immediately before use, the resulting composition being applied on the hair for 5 to 40 minutes, and preferably 20 to 30 minutes. The hair is then rinsed, washed with shampoo, rinsed again and thereafter dried.

According to another variant, the process of the invention consists in applying on the hair at least one component (A) and, before or after the component (A), a component (B), as are defined above; and in leaving each component in place for 5 to 40 minutes, and preferably 20 to 30 minutes, optionally rinsing with water between the two steps. The hair is then rinsed, washed with shampoo, rinsed again and thereafter dried.

The examples which follow are designed to illustrate the invention, no limitation of the latter, however, being implied.

EXAMPLES 1 TO 4

Hair dyeing is performed by applying 20 g of the compositions on natural grey hair which is 90% white.

The compositions are prepared immediately before use.

The composition is left to act for 20 minutes, the hair is then rinsed, shampooing is performed and the hair is then rinsed again. After drying, the hair is dyed in the hue specified at the bottom of Table I below.

TABLE I

|  | In g AS | | | |
|---|---|---|---|---|
|  | 1 | 2 | 3 | 4 |
| Isatin | 1 | 1 | 0.5 | 1 |
| Tetraaminopyrimidine | 1 | | 0.5 | |
| 2,5-Diaminopyridine | | 1 | | |
| 2-Aminopyridine | | | | 1 |
| Ethylene alcohol | 30 | 30 | 30 | 30 |
| Sodium lauryl ether sulphate oxyethylenated with 2 mol of ethylene oxide, containing 28% of AS | | | 8.4 | |
| Triethanolamine qs pH | 7.6 | 7.3 | 8 | 8.6 |
| Water qs | 100 | 100 | 100 | 100 |
| Hues obtained | coppery red | coppery brown | coppery iridescent | intense golden coppery |

EXAMPLES 5 TO 7

Hair dyeing is performed by applying 20 g of the compositions on permanent-waved grey hair which is 90% white.

The compositions are prepared immediately before use.

The composition is left to act for 20 minutes and the hair is then rinsed (in Example 7, shampooing is then performed and the hair is thereafter rinsed again). After drying, the hair is dyed in the hue specified at the bottom of Table II below.

EXAMPLE 8

The dyeing of permanent-waved grey hair which is 90% white is performed.

5 g of the composition A are applied on 3 g of hair for 15 minutes, the composition A being diluted before use with 3 times its weight of water.

After rinsing of the hair, 8 g of the composition B are applied for 15 minutes, the composition B being diluted with 1.5 times its weight of water before use.

The hair is then rinsed and thereafter dried.

At the end, a coloration is obtained the hue of which is shown in Table II below.

TABLE II

|  | In g AS | | | | |
|---|---|---|---|---|---|
|  |  |  |  | 8 | |
|  | 5 | 6 | 7 | Comp. A | Comp. B |
| Isatin | 1 | 1 |  | 4 |  |
| 5-Chloroisatin |  |  | 0.25 |  |  |
| 2,6-Dimethoxy-3,5-diaminopyridine | 1 |  |  |  |  |
| 6-Methoxy-2,3-diaminopyridine |  | 1 | 0.25 |  | 1 |
| Carob gum sold by the company Sanofi Bio Industrie under the name Vidogum L 175 |  |  | 3 |  |  |
| Calcium carbonate |  |  |  | 8 |  |
| Powdered residues of exhaustive extraction of Saponaria, of particle size less than 90 microns |  |  |  | 35 |  |
| Skimmed milk powder qs |  |  | 100 |  |  |
| Ethyl alcohol | 30 | 30 | 30 |  | 28.5 |
| Sodium lauryl ether sulphate oxyethylenated with 2 mol of ethylene oxide, containing 28% of AS |  |  | 8.4 |  |  |
| Triethanolamine |  |  |  |  | 1 |
| Nonylphenol oxyethylenated with 9 mol of ethylene oxide qs |  |  |  |  | 100 |
| Triethanolamine qs pH | 8 | 8 | 8 |  |  |
| Water qs | 100 | 100 | 100 |  |  |
| Hues obtained | golden matt blond | intense red | iridescent light blond |  | iridescent very light blond |

We claim:

1. A process for dyeing keratinous fibers comprising applying to said fibers a component (A) comprising a composition containing, in a medium suitable for dyeing said fibers, at least one compound of formula (I)

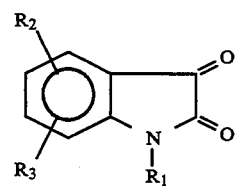

(I)

wherein
$R_1$ represents hydrogen, $C_1$–$C_6$ alkyl, acetyl, benzoyl, phenyl or $C_1$–$C_4$ carboxyalkyl,
$R_2$ and $R_3$, each independently, represent hydrogen, $C_1$–$C_6$ alkyl, hydroxyl, halogen, nitro, ($C_1$–$C_6$ alkyl) phenyl, phenyl or $C_1$–$C_4$ alkoxy, and a component (B) comprising a composition containing, in a medium suitable for dyeing said fibers, at least one aminopyrimidine of formula (III),

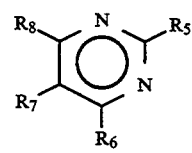

(III)

wherein
$R_5$ represents hydrogen, hydroxyl or

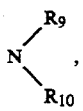

$R_6$ represents hydroxyl or

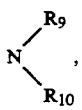

$R_7$ represents H or $NH_2$,
$R_8$ represents

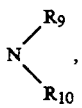

$R_9$ and $R_{10}$, each independently, represent hydrogen, $C_1$–$C_4$ alkyl, $(CH_2)_p$-Z wherein p=1 to 4 and Z represents OH, halogen, $NH_2$, NHR' or NHR'R" wherein R' and R" represent $C_1$–$C_4$ alkyl or together with the nitrogen atom to which they are attached form a heterocycle, said compound of formula (I) being present in said component (A) in an amount ranging from 0.01 to 5 percent by weight based on the total weight of said component (A) or to the total weight of component (A) plus component (B), and said compound of formula (III) being present in said component (B) in an amount ranging from 0.01 to 5 percent by weight based on the total weight of said component (B) or to the total weight of component (A) plus component (B), with the proviso that one of $R_5$ to $R_8$ represents $NH_2$; and the cosmetically acceptable salts thereof.

2. The process of claim 1 wherein said compound of formula (III) is selected from
5,6-diamino-2,4-dihydroxypyrimidine,
4,6-diaminopyrimidine,
2,4,5,6-tetraaminopyrimidine.

3. The process of claim 1 wherein said component (A) or said component (B), or both, is an aqueous or anhydrous composition in thickened liquid form or a composition in the form of a cream, an aqueous or anhydrous gel, an oil or a powder to be diluted with a liquid at the time of use.

4. The process of claim 3 wherein said component (A) or said component (B), or both, is in the form of an aqueous composition having a pH ranging from 2 to 10, said aqueous composition also containing at least one cosmetically acceptable adjuvant selected from an anionic, cationic or nonionic surfactant, or a mixture thereof; an organic solvent; an anionic, nonionic, cationic or amphoteric polymer, or a mixture thereof; a thickening agent; a penetrating agent; a sequestering agent; an antioxidant; a buffer; a dye; and a perfume.

5. The process of claim 3 wherein said component (A) or said component (B), or both, is in the form of an anhydrous composition containing at least one anhydrous solvent present in an amount of at least 15 weight percent and at least one anhydrous surfactant present in an amount of at least 20 weight percent.

6. The process of claim 5 wherein said anhydrous solvent is selected from a saturated $C_2$–$C_{20}$ monohydric alcohol, a polyol, a glycol ether, a glycol ester and an ester of a fatty acid and a lower alcohol.

7. The process of claim 3 wherein said component (A) or said component (B), or both, is in the form of a powder to be diluted with a liquid at the time of use, said powder comprising an amylaceous or mucilaginous substance, a silica, a clay or a powdered plant material, the active principles of which have been solvent-extracted.

8. The process of claim 7 which includes adding a cosmetically acceptable liquid to said component (A) or said component (B), or both, in powder form, so as to produce a cataplasm having a viscosity of 0.3 to 5 Pa.s.

9. The process of claim 1 wherein said components (A) and (B) are mixed immediately before application to said fibers and the resulting mixture is immediately applied to said fibers and wherein said mixture is permitted to remain in contact with said fibers for a period of time ranging from 5 to 40 minutes, after which said fibers are rinsed, shampooed, rinsed and dried.

10. The process of claim 1 wherein the application of said component (A) to said fibers is preceded by or followed by the application of said component (B) to said fibers, said fibers optionally being rinsed with water intermediate the application of said components to said fibers, and each of said component (A) and component (B) being permitted to remain in contact with said fibers for a period of time ranging from 5 to 40 minutes, after which said fibers are rinsed, shampooed, rinsed and dried.

11. A dyeing agent for keratinous fibers comprising components (A) and (B) as defined in claim 1, in separate form to be admixed together immediately before use or to be successively applied to said fibers to be dyed.

12. A multi-compartment device or "dyeing kit" comprising at least two compartments, a first of which contains a component (A) as defined in claim 1 and a second of which contains a component (B) as defined in claim 1.

13. The device of claim 12 wherein said component (A) or said component (B), or both, as in the form of an anhydrous composition and said device includes a third compartment containing a cosmetically acceptable aqueous medium suitable for dyeing keratinous fibers and intended to be mixed before use with one or both of the contents of said first and second compartments.

* * * * *